(12) United States Patent
Hirst

(10) Patent No.: US 8,533,887 B2
(45) Date of Patent: Sep. 17, 2013

(54) APPARATUS FOR DISINFECTING HANDHELD INSTRUMENTS

(75) Inventor: Sandra Hirst, Kaysville, UT (US)

(73) Assignee: Sandra B. Hirst, E. Kaysville, UT (US)

( * ) Notice: Subject to any disclaimer, the term of this patent is extended or adjusted under 35 U.S.C. 154(b) by 352 days.

(21) Appl. No.: 12/975,721

(22) Filed: Dec. 22, 2010

(65) Prior Publication Data

US 2011/0146012 A1   Jun. 23, 2011

Related U.S. Application Data

(60) Provisional application No. 61/289,743, filed on Dec. 23, 2009.

(51) Int. Cl.
*A47L 13/17*    (2006.01)
*A47L 25/00*    (2006.01)

(52) U.S. Cl.
USPC ............... 15/104.92; 15/104.94; 15/220.4

(58) Field of Classification Search
USPC ............. 15/104.93, 104.94, 218.1, 220.4, 15/244.1, 104.92; 206/205
See application file for complete search history.

(56) References Cited

U.S. PATENT DOCUMENTS

| | | | |
|---|---|---|---|
| 1,767,954 A * | 6/1930 | Adam | 15/220.4 |
| 4,282,891 A | 8/1981 | Duceppe | |
| 4,446,965 A | 5/1984 | Montiel | |
| 5,722,537 A | 3/1998 | Sigler | |
| 6,036,490 A * | 3/2000 | Johnsen et al. | 433/102 |
| 6,142,297 A | 11/2000 | Price | |
| 6,379,066 B1 | 4/2002 | Gomez | |
| 7,041,261 B2 | 5/2006 | Margolis | |
| 2004/0191141 A1 | 9/2004 | Margolis | |
| 2010/0064456 A1 * | 3/2010 | Ferlic | 15/104.94 |

* cited by examiner

*Primary Examiner* — Randall Chin
(74) *Attorney, Agent, or Firm* — Chad Nydegger

(57) ABSTRACT

A sanitizer for disinfecting substantially the entire outer surface of a handheld instrument comprises a container having a well therein for holding a disinfectant and a passageway by which the handheld instrument may be inserted into the well. The sanitizer may include a first opening and a second opening, the openings being located at opposing ends of the passageway such that the handheld instrument may enter the sanitizer through the first opening, and exit the sanitizer through the second opening. The sanitizer may further include an absorbent material located in the well to disperse the disinfectant on the outer surface of the handheld instrument, and to prevent the disinfectant from leaking from the well during use.

19 Claims, 5 Drawing Sheets

APPARATUS FOR DISINFECTING HANDHELD INSTRUMENTS

CROSS-REFERENCE TO RELATED APPLICATIONS

The present application claims benefit of and priority from provisional application Ser. No. 61/289,743 filed 23 Dec. 2009. The disclosures of the above-mentioned application are hereby incorporated by reference in their entireties.

BACKGROUND OF THE INVENTION

Preventing the spread of disease throughout a population is a significant problem. For example, in 2009 the world experienced the H1N1 flu virus pandemic during which the H1N1 flu virus quickly traversed states, countries and continents to infect persons throughout the world. Diseases such as the H1N1 flu virus are often spread from one person to another person by innate objects. For example, a person infected with a disease may cough into their hands, and then touch an innate object such as a door knob, thereby contaminating the door knob with disease causing germs. The hands of subsequent persons who touch that door knob will be contaminated with the disease-causing germs left on the door knob by the previous person, and may subsequently become sick as a result thereof.

Handheld instruments or tools, such as writing instruments, are another common vehicle for spreading disease-causing germs, such as the H1N1 virus. For example, a cashier working at a cash register of a grocery store may lend his or her pen to hundreds of different customers during a single day, each of whom may use the pen to sign a credit card receipt to pay for his or her respective groceries. Each person who touches the pen may contaminate the outer surface of the pen with disease-causing germs and/or become contaminated with disease-causing germs already present on the surface of the pen from a person who previously used the pen. Thus, handheld instruments such as pens have become common vehicles for spreading disease.

Recognizing that the surfaces of handheld instruments may be vehicles for passing diseases from one user to another, many individuals now carry liquid disinfectants. Individuals that use such liquid disinfectants typically dispense the disinfectant into the palm of one hand, and then spread the disinfectant over the entire surface of both hands by rubbing his or her hands together. Frequent use of such liquid disinfectants, however, may be undesirable because such disinfects can dry out and/or irritate the skin if used too frequently. Additionally, a user of such a liquid disinfectant typically uses a sufficient amount of disinfectant to disinfect his or her entire hands, even though only a small portion of a single hand may have become contaminated by touching a contaminated object.

An alternative approach to preventing the spread of disease through sharing handheld instruments is desired. Accordingly, what is desired is an apparatus for disinfecting handheld instruments. The apparatus may be used to repeatedly disinfect one or more handheld instruments by dispersing a disinfecting medium on a handheld instrument passed through the device. Optionally, the apparatus may include a well to hold the disinfectant, the well being refillable. In one embodiment, the apparatus may also wipe excess disinfectant from the handheld tool as it is disinfected.

BRIEF SUMMARY

Embodiments of the present disclosure are directed to an apparatus for disinfecting handheld instruments. More particularly, embodiments of the present disclosure relate to an apparatus through which handheld instruments are passed such that substantially the entire outer surface of the instrument is disinfected.

According to one embodiment, the apparatus includes first and second openings located on opposing ends of a container. The container includes a well for holding a liquid disinfectant, and an absorbent material that prevents the liquid disinfectant from exiting the openings. A handheld instrument is inserted into the first opening, passed through the well of the container, and exits the second opening. As the handheld instrument passes through the well of the container, the absorbent material disperses a sufficient amount of the disinfectant over the outer surface of the handheld instrument to disinfect the handheld instrument.

In one embodiment, the first and second openings may also be deformable such that the opening deforms to the shape of the handheld instrument as the instrument passes through the second opening. In this embodiment the second opening may be configured to wipe excess disinfectant from the handheld instrument as it passes through the second opening.

Optionally, the sanitizing apparatus may include a clip for attaching the sanitizing apparatus to a stand, lanyard, article of clothing, or other object. In another embodiment the sanitizing agent may optionally include a bracket for securing the sanitizing apparatus to a wall, counter, cabinet or other surface.

In another embodiment, the apparatus includes a container with a first opening and a well for holding a disinfectant. This embodiment may also include an ejector for ejecting the handheld instrument back out of the first opening through which the handheld instrument passed to enter the container.

Additional features and advantages of the embodiments disclosed herein will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

BRIEF DESCRIPTION OF THE DRAWINGS

To further clarify various aspects of embodiments of the present disclosure, a more particular description of the disclosure will be rendered by reference to specific embodiments thereof which are illustrated in the appended drawings. It is appreciated that these drawings depict only typical embodiments of the disclosure and are therefore not to be considered limiting of its scope, nor are the figures necessarily drawn to scale. The embodiments of the present disclosure will be described and explained with additional specificity and detail through the use of the accompanying drawings in which.

DETAILED DESCRIPTION

Example embodiments of the present disclosure are directed to devices for disinfecting handheld instruments. More particularly, exemplary embodiments of the present disclosure are directed to devices for sanitizing substantially the entire outer surface of handheld instruments in an efficient and economical manner.

With reference now to FIGS. 1 through 4, an embodiment of a sanitizer 100 for disinfecting handheld tools is illustrated. For convenience, like parts in each of these Figures shall be referenced with same numbers.

Figure 1:
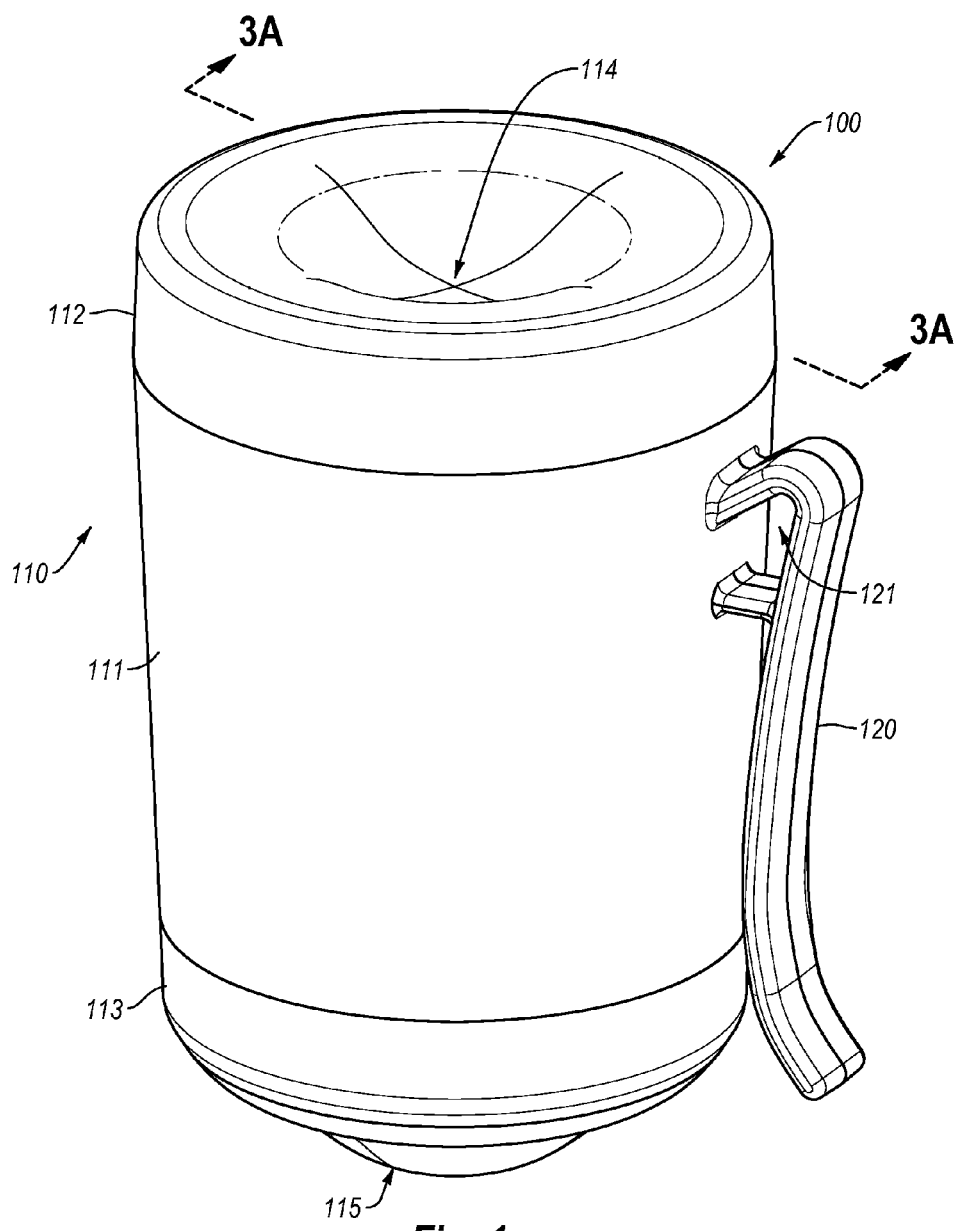
FIG. 1 illustrates a perspective view of an example embodiment of a sanitizing apparatus for disinfecting handheld instruments.
Figure 3A:
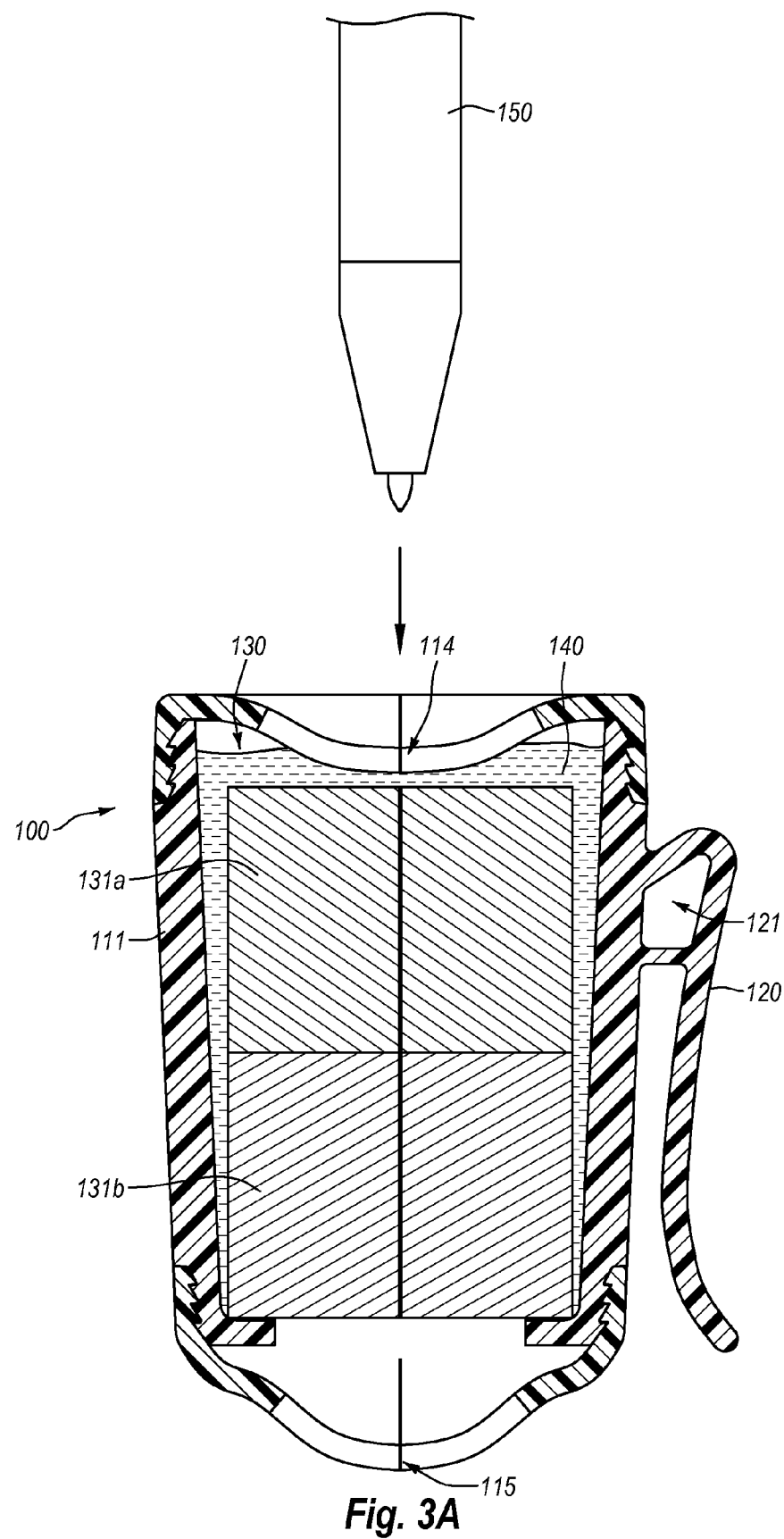
FIG. 3A illustrates a cross-sectional view of an example embodiment of a sanitizing apparatus for disinfecting handheld instruments prior to a handheld instrument being introduced into the sanitizing apparatus.

Turning to FIG. 1, the sanitizer 100 has a container 110. The container 110 includes a body 111 forming a solid outer shell. Body 111 may be made of plastic, metal, or any other suitable material that is impermeable by a disinfecting medium. Container 110 further includes a top cap 112 and bottom cap 113 connected to body 111 on opposing ends thereof. Top cap 112 and bottom cap 113 are retained on body 111 by any conventional method known in the art, including compression fit, threads, clamps, adhesives, welds, etc. In one embodiment, top cap 112 and bottom cap 113 are selectively removable from body 111. In another embodiment, one or both of caps 112 and 113 are permanently attached to body 111. In yet another embodiment, top cap 112 and bottom cap 113 are integrated with body 111. In one embodiment, top cap 112 and bottom cap 113 are made of a flexible material, such as rubber or plastic. When top cap 112 and bottom cap 113 are attached to body 111 the container forms a well 130 (FIG. 3A). Well 130 may take any shape or configuration. In one embodiment, top cap 112 and bottom cap 113 each have an opening therein, shown as 114 and 115, respectively.

In one embodiment, body 111 also includes a clip 120. Clip 120 may be used to attach the sanitizer to clothing, a clip board, a stand, or any other number of articles as conventionally known in the art. Clip 120 may be further configured such that clip 120 forms an enclosure with an opening 121 that may be used to attach sanitizer 100 to a lanyard, key chain ring, carabiner or any number of other items.

Figure 2:
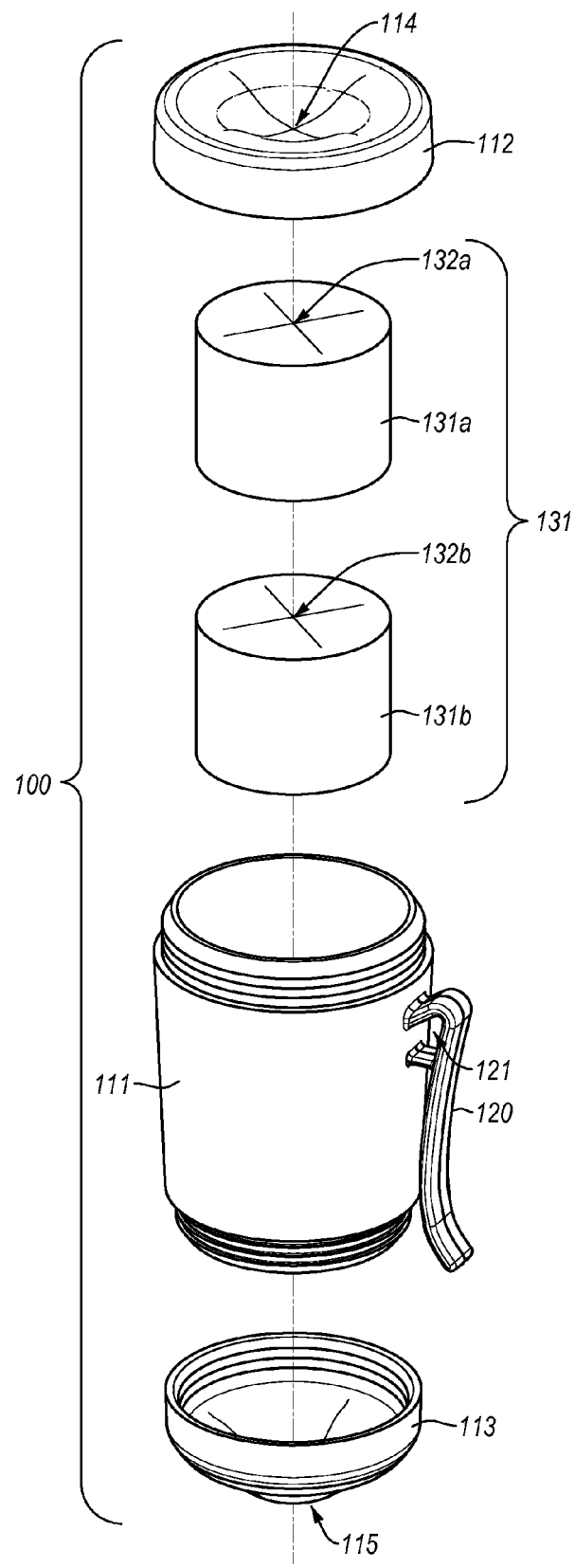
FIG. 2 illustrates an exploded view of an example embodiment of a sanitizing apparatus for disinfecting handheld instruments.

Referring now to FIG. 2, sanitizer 100 includes an absorbent material 131. Absorbent material 131 is placed in well 130. Absorbent material 131 is capable of retaining a disinfectant 140 (FIG. 3A) within container 110 and of dispersing the disinfectant 140 on the outer surface of a handheld instrument 150 (FIG. 3A) as the handheld instrument 150 is passed through sanitizer 100. Absorbent material 131 may be made of cloth, sponge, such as felted polyurethane sponge, or any other material capable of absorbing disinfectant 140 and dispersing disinfectant 140 on the outer surface of handheld instrument 150 as the handheld instrument 150 is passed through sanitizer 100. Absorbent material 131 has a passageway, shown in FIG. 2 as 132a and 132b, through which a handheld instrument 150 may be passed (see FIG. 3B). The passageway formed by 132a and 132b may be of any shape or configuration so long as substantially the entire outer surface of a handheld instrument 150 is coated with disinfectant 140 as handheld instrument 150 passes through the passageway. In one embodiment, absorbent material 131 includes any number of pieces configured such that the pieces are displaced by handheld instrument 150 as it is passed through the container. In this embodiment, handheld instrument 150 forms a passageway as it passes through container 110 by displacing pieces of absorbent material 131 located within well 130. In another embodiment, the absorbent material is rolled or folded to form the passageway.

In another embodiment, absorbent material 131 includes a number of substantially horizontal flanges (not shown) arranged in concentric rings placed parallel to top cap 112 and bottom cap 113, the flanges being spaced throughout the container 110 such that the viscosity of disinfectant 140 substantially retains any excess disinfectant 140 between the flanges and within container 110 as a handheld instrument 150 is passed through the container 110. The flanges are further configured such that they form a passageway through which a handheld instrument 150 may pass, and such that the flanges disperse disinfectant 140 on substantially the entire surface of handheld instrument 150 as handheld instrument 150 is passed through the passageway. In this embodiment, the configuration of the flanges retains the disinfectant 140 within the container 110 as handheld instrument 150 is passed through container 110, and, therefore, the flanges do not need to be made of a material capable of absorbing the disinfectant 140.

Referring to FIG. 3A, a cross section of the sanitizer 100 of FIGS. 1 and 2 is shown prior to handheld instrument 150 being inserted into sanitizer 100 is illustrated. Container 100 has a well 130 to hold disinfectant 140. Disinfectant 140 may be a liquid hand sanitizer, rubbing alcohol, or any other suitable disinfecting medium currently known in the art, or that becomes known in the art in the future. In one embodiment, well 130 may be refilled with disinfectant 140 at any time it contains insufficient disinfectant 140 to disinfect a handheld instrument 150 that is passed through container 110. Absorbent material 131a and 131b help prevent disinfectant 140 from leaking out of openings 114 and 115. Additionally, in one embodiment openings 114 and 115 are substantially closed to prevent disinfectant 140 from evaporating or drying out when the sanitizer is not in use.

Figure 3B:
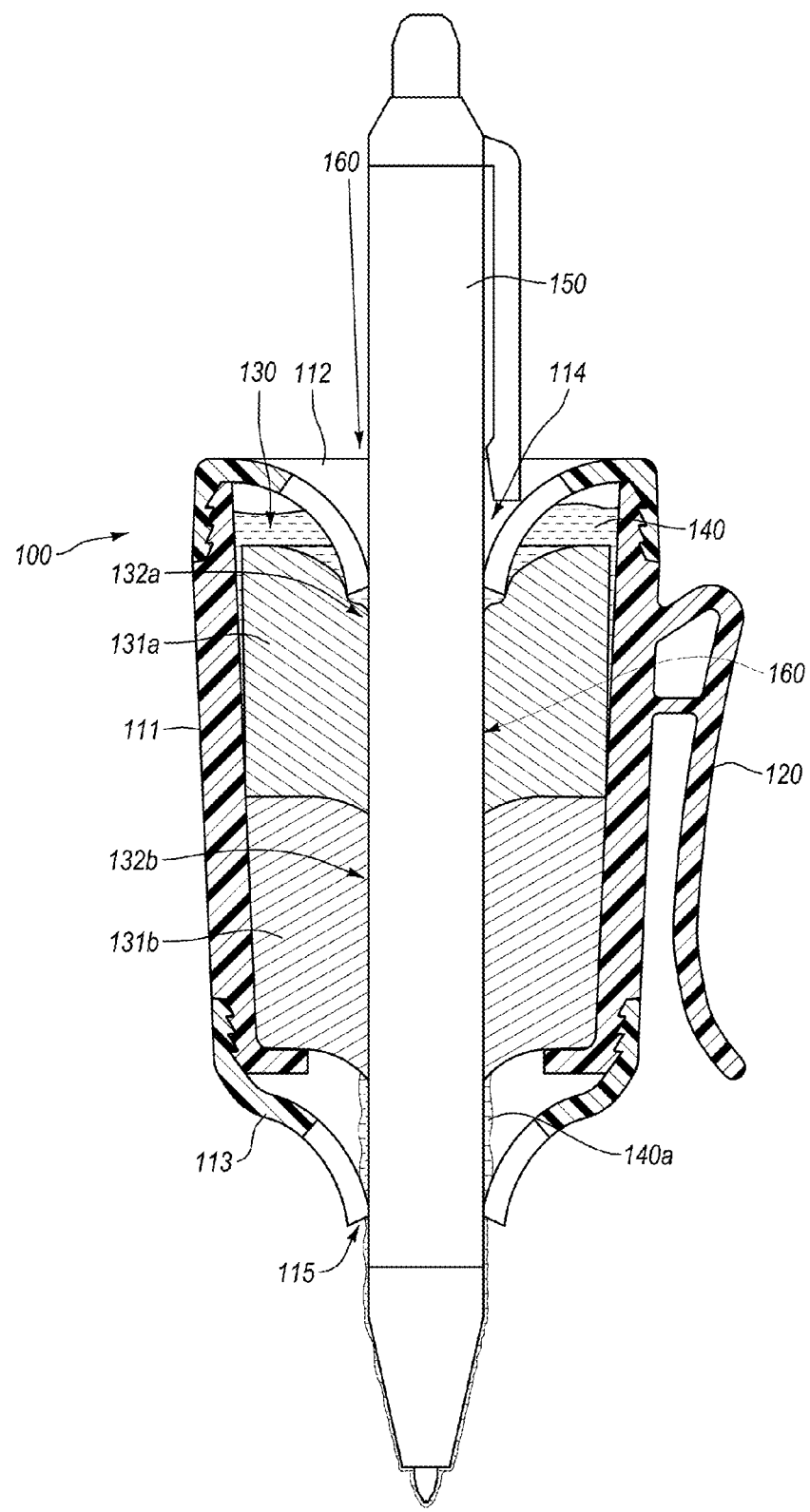
FIG. 3B illustrates a cross-sectional view of an example embodiment of a sanitizing apparatus for disinfecting handheld instruments with a handheld instrument passing through the sanitizing apparatus.

Referring to FIG. 3B, a cross section of the sanitizer 100 of FIGS. 1, 2 and 3A is shown during use with handheld instrument 150 passing through sanitizer 100 is illustrated. During use, a first user inserts the handheld instrument into sanitizer 100 by passing an end of the handheld instrument through the opening 114 in top cap 112, through the passageways 132a and 132b, until the end of handheld instrument 150 projects from opening 115 in bottom cap 113, as shown in FIG. 3B. Once the handheld instrument has reached the approximate position with respect to sanitizer 100 as shown in FIG. 3B, a second user removes the handheld instrument from the sanitizer 100 by pulling the end of handheld instrument 150 protruding from opening 115 in bottom cap 113 until the remaining portion of handheld instrument 150 exits sanitizer 100 by passing there through. By transferring handheld instrument 150 from the first user to the second user in the described manner, the second user is not required to touch any part of handheld instrument 150 that has not been disinfected by passing through sanitizer 100. Alternatively, a single user may both insert handheld instrument 150 into, and remove handheld instrument 150 from, sanitizer 100 in the manner described, thereby disinfecting handheld instrument 150.

In one embodiment, openings 114 and 115 expand or deform as handheld instrument 150 comes into contact with openings 114 and 115. In this embodiment, openings 114 and 115 allow handheld instrument 150 to pass through openings 114 and 115, but also substantially conforming to the surface of handheld instrument 150 so that disinfectant 140 does not leak out of openings 114 and 115 as handheld instrument 150 is passed there through. In one embodiment, openings 114 and 115 are configured such that absorbent material 131 is not required because openings 114 and 115 sufficiently retain disinfectant 140 within well 130 without the assistance of absorbent material 131.

FIG. 3B also illustrates how handheld instrument 150 passes through a passageway 160 formed by opening 114, passageways 132a and 132b, and opening 115. As handheld instrument 150 passes through passageway 160, a coating 140a of disinfectant 140 is dispersed along substantially the entire surface of handheld instrument 150. As handheld instrument 150 exits the sanitizer 100 by passing through opening 115, opening 115 substantially conforms to the shape of handheld instrument 150 such that excess disinfectant 140 is wiped off of handheld instrument 150. After passing through opening 115, handheld instrument 150 has been substantially disinfected, and substantially all of the excess disinfectant 140 has been retained within sanitizer 100.

In one embodiment, container 110 is configured such that well 130 may be refilled with disinfectant 140 as disinfectant 140 is consumed through use. For example, top cap 112 or bottom cap 113 may be removable to allow well 130 to be refilled with disinfectant 140. In another embodiment, well 130 may be refilled with disinfectant 140 through opening 114, opening 115 or through a separate opening (not shown) configured specifically to allow well 130 to be refilled.

In another embodiment not depicted, the handheld instrument may enter the container and exit the container through the same opening. In this embodiment, the container is sized and configured such that substantially the entire handheld instrument may fit inside container. This embodiment further includes an ejector for ejecting the handheld instrument back out of the opening in the container through which the handheld instrument was introduced into the container. Such an ejector may utilize a spring, lever, or other mechanical ejector as conventionally known.

Figure 4:
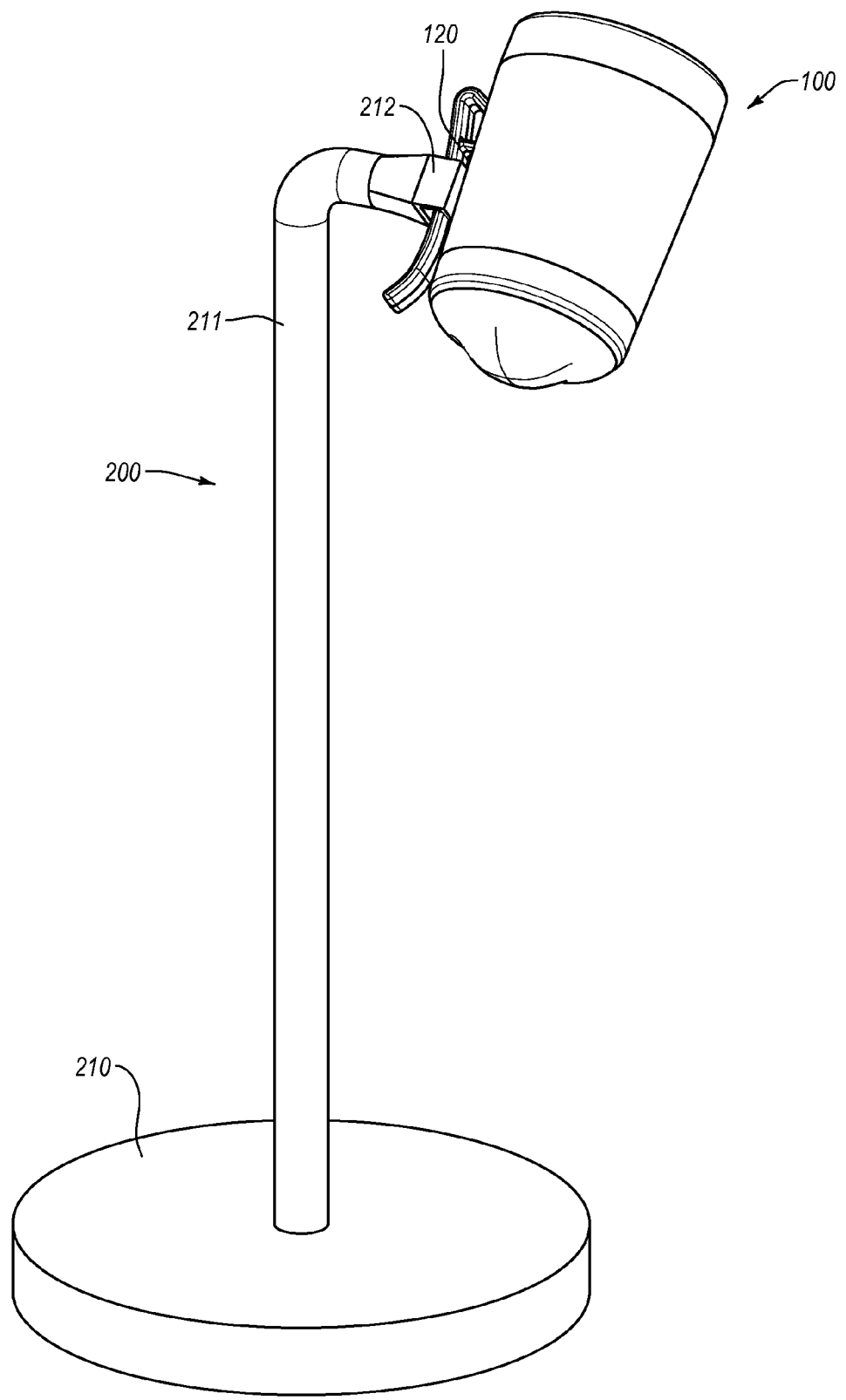
FIG. 4 illustrates a perspective view of an example embodiment of a sanitizing apparatus for disinfecting handheld instruments connected to an example embodiment of stand for the same.

Referring to FIG. 4, the sanitizer 100 of FIGS. 1 through 3B is illustrated connected to a stand 200. Stand 200 includes a base 210 for placement on a horizontal surface, such as a countertop or desk, and a vertical member 211 extending in a substantially vertical direction from base 210. Attached to vertical member 211 is a connector 212 configured to removably connect to clip 120 of sanitizer 100. Thus, stand 200 stably retains sanitizer 100 during use. In another embodiment, sanitizer 100 is connected to stand 200 such that sanitizer 100 is not removable from stand 200.

In another embodiment, not shown, sanitizer 100 includes a bracket that can be securely fastened to a vertical surface, such as a wall or cabinet. In one embodiment, the bracket can be configured as an integral part of container 110. In another embodiment, the bracket may contain a connector such that sanitizer 100 can be removably connected to the bracket in a fashion similar to that of the removable connection between sanitizer 100 and base 200 shown in FIG. 4.

In another embodiment, the sanitizer is configured with multiple openings in both the top and bottom caps such that multiple handheld instruments may be placed in the sanitizer simultaneously. In this embodiment, the sanitizer functions in the same manner as that described above in connection with FIGS. 1 through 4.

Although the foregoing embodiments have been described in some detail by way of illustration and example, for purposes of clarity and understanding, certain changes and modifications will be obvious to those with skill in the art in view of the disclosure herein. The described embodiments are to be considered in all respects only as illustrative and not restrictive. Thus, all changes which come within the meaning and range of equivalency of the claims are to be embraced within their scope.

What is claimed is:

1. A sanitizer for disinfecting the outer surface of a handheld instrument, the sanitizer comprising:
   a container comprising:
      a body;
      a first opening configured for a handheld instrument to pass there through to enter the container;
      a second opening configured for the handheld instrument to pass there through to exit the container, wherein the second opening is configured to deform upon the application of pressure exerted on the second opening by the handheld instrument as the handheld instrument exits the container through the second opening; and
      wherein the container forms a well for holding a disinfectant; and
   an absorbent material located in the well, the absorbent material configured to substantially retain the disinfectant within the well and to disperse a portion of the disinfectant on substantially the entire outer surface of the handheld instrument to substantially disinfect the handheld instrument as the handheld instrument passes through the container.

2. The sanitizer for disinfecting the outer surface of a handheld instrument defined in claim 1, wherein the absorbent material forms a passageway through the container and extending from approximately the first opening through the absorbent material to approximately the second opening;
   wherein the absorbent material is configured to disperse a portion of the disinfectant on substantially an entire outer surface of the handheld instrument as the handheld instrument passes through the passageway;
   and wherein the absorbent material retains substantially all excess disinfectant in the well as the handheld instrument passes through the passageway.

3. The sanitizer for disinfecting the outer surface of a handheld instrument defined in claim 2, wherein the absorbent material comprises at least one sponge.

4. The sanitizer for disinfecting the outer surface of a handheld instrument defined in claim 3, wherein the passageway through the absorbent material is formed by at least one slit in the at least one sponge.

5. The sanitizer for disinfecting the outer surface of a handheld instrument defined in claim 3, further comprising a bracket for attaching the refillable sanitizer to a wall.

6. The sanitizer for disinfecting the outer surface of a handheld instrument defined in claim 3, the container further comprising a first end with a selectively removable cap.

7. The sanitizer for disinfecting the outer surface of a handheld instrument defined in claim 3, the second opening further sized and configured to wipe substantially all excess disinfectant from the outer surface of the handheld instrument as the handheld instrument exits the container.

8. The sanitizer for disinfecting the outer surface of a handheld instrument defined in claim 7, further comprising a clip.

9. The sanitizer for disinfecting the outer surface of a handheld instrument defined in claim 1, further comprising:
   a disinfectant; and
   wherein the absorbent material comprises at least two flanges;
   wherein the at least two flanges are configured to form a passageway through the container and extending from approximately the first opening, through the at least two flanges, to approximately the second opening;

wherein at least one flange of the at least two flanges is further configured to disperse a portion of the disinfectant on substantially an entire outer surface of the handheld instrument as the handheld instrument passes through the passageway; and wherein the at least two flanges are spaced apart such that the viscosity of the disinfectant retains substantially all excess disinfectant inside the well as the handheld instrument passes through the passageway.

10. The sanitizer for disinfecting the outer surface of a handheld instrument defined in claim 9, the container further comprising a first end with a selectively removable cap.

11. The sanitizer for disinfecting the outer surface of a handheld instrument defined in claim 9, the second opening further sized and configured to wipe substantially all excess disinfectant from the outer surface of the handheld instrument as the handheld instrument exits the container.

12. The sanitizer for disinfecting the outer surface of a handheld instrument defined in claim 11, further comprising a clip.

13. The sanitizer for disinfecting the outer surface of a handheld instrument defined in claim 1, wherein the first opening is configured to deform upon the application of pressure exerted on the first opening by the handheld instrument as the handheld instrument is inserted into the first opening.

14. The sanitizer for disinfecting the outer surface of a handheld instrument defined in claim 13, the container further comprising a first end with a selectively removable cap.

15. The sanitizer for disinfecting the outer surface of a handheld instrument defined in claim 1, the second opening further sized and configured to wipe substantially all excess disinfectant from the outer surface of the handheld instrument as the handheld instrument exits the container.

16. The sanitizer for disinfecting the outer surface of a handheld instrument defined in claim 15, further comprising a clip.

17. A sanitizer for disinfecting the outer surface of a handheld instrument, the sanitizer comprising:
a container comprising:
a body;
a first opening configured for a handheld instrument to pass there through to enter the container;
a second opening configured for the handheld instrument to pass there through to exit the container; and
wherein the container forms a well for holding a disinfectant; and
an absorbent material located in the well, the absorbent material configured to substantially retain the disinfectant within the well and to disperse a portion of the disinfectant on substantially the entire outer surface of the handheld instrument to substantially disinfect the handheld instrument as the handheld instrument passes through the container; and
a stand, comprising:
a base member for placement on a horizontal surface; and
an arm extending upwardly from the base member;
wherein the container is attached to the arm; and
wherein the stand is sized and configured to stably hold the container as a handheld instrument is passed through the container.

18. A kit for disinfecting a handheld instrument, comprising:
a container comprising:
a body;
a first opening configured for a handheld instrument to pass there through to enter the container;
a second opening configured for a handheld instrument to pass there through to exit the container, wherein the second opening is configured to deform upon the application of pressure exerted on the second opening by the handheld instrument as the handheld instrument exits the container; and
wherein the container forms a well for holding a disinfectant; and
an absorbent material configured to substantially retain the disinfectant within the well and to disperse a portion of disinfectant on substantially the entire outer surface of the handheld instrument to substantially disinfect the handheld instrument as the handheld instrument passes through the container.

19. The kit for disinfecting the outer surface of a handheld instrument defined in claim 18, further comprising a disinfectant.

* * * * *